United States Patent
Chiu et al.

(10) Patent No.: US 8,969,634 B2
(45) Date of Patent: Mar. 3, 2015

(54) COMBINATION REACTOR SYSTEM

(75) Inventors: Yuon Chiu, Denville, NJ (US); Haluk Kopkalli, Staten Island, NY (US); Richard Durick Horwath, Morristown, NJ (US)

(73) Assignee: Honeywell International Inc., Morristown, NJ (US)

( * ) Notice: Subject to any disclaimer, the term of this patent is extended or adjusted under 35 U.S.C. 154(b) by 74 days.

(21) Appl. No.: 13/245,328

(22) Filed: Sep. 26, 2011

(65) Prior Publication Data

US 2013/0079563 A1    Mar. 28, 2013

(51) Int. Cl.
| | | |
|---|---|---|
| C07C 17/00 | (2006.01) | |
| C07C 21/00 | (2006.01) | |
| C07C 17/354 | (2006.01) | |
| B01J 8/04 | (2006.01) | |
| B01J 8/06 | (2006.01) | |

(52) U.S. Cl.
CPC .............. *C07C 17/354* (2013.01); *B01J 8/048* (2013.01); *B01J 8/0492* (2013.01); *B01J 8/0496* (2013.01); *B01J 8/065* (2013.01); *B01J 8/067* (2013.01); *B01J 2208/00221* (2013.01); *B01J 2208/00902* (2013.01); *B01J 2208/00929* (2013.01)
USPC ........................................................ 570/175

(58) Field of Classification Search
CPC ................................................... C07C 17/354
See application file for complete search history.

(56) References Cited

U.S. PATENT DOCUMENTS

| | | | |
|---|---|---|---|
| 2,990,348 A | * | 6/1961 | Wollan ........................ 376/177 |
| 3,566,961 A | | 3/1971 | Lorenz et al. |
| 3,792,980 A | | 2/1974 | Vollmer et al. |
| 4,101,287 A | | 7/1978 | Sweed et al. |
| 4,929,798 A | | 5/1990 | de Lasa |
| 5,027,891 A | | 7/1991 | Fulford et al. |
| 6,180,846 B1 | | 1/2001 | Dandekar et al. |
| 6,790,431 B2 | | 9/2004 | Wang et al. |
| 7,521,028 B2 | | 4/2009 | Smith et al. |
| 2004/0267063 A1 | * | 12/2004 | Harth et al. .................. 570/224 |
| 2007/0043126 A1 | | 2/2007 | Lattner |
| 2008/0315151 A1 | | 12/2008 | Suppes et al. |

(Continued)

FOREIGN PATENT DOCUMENTS

EP        0792683    *    9/1997    ............... B01J 19/18

OTHER PUBLICATIONS

Trickle Bed Reactor Developed by Research Institute of Jilin Chemical Company, China Petroleum Processing and Petrochemical Technology, No. 2, p. 20, Jun. 2004 (1 page).

(Continued)

*Primary Examiner* — Clinton Brooks
(74) *Attorney, Agent, or Firm* — Bruce O. Bradford

(57) ABSTRACT

The present invention is directed to a combination reactor system for exothermic reactions comprising a trickle-bed reactor and a shell-and-tube reactor. This combination allows the system to efficiently remove heat while also providing the ability to control both the temperature and/or reaction progression. The trickle-bed reactor removes heat efficiently from the system by utilizing latent heat and does not require the use of a cooling or heating medium. The shell-and-tube reactor is used to further progress the reaction and provides a heat exchanger in order to introduce fluid at the desired temperature in the shell-and-tube reactor. Also, additional reactant or reactants and/or other fluids may be introduced to the shell-and-tube section of the reactor under controlled temperature conditions.

10 Claims, 3 Drawing Sheets

(56) References Cited

U.S. PATENT DOCUMENTS

| | | |
|---|---|---|
| 2009/0171109 A1 | 7/2009 | Benderly et al. |
| 2009/0234165 A1* | 9/2009 | Chiu et al. .................... 570/136 |
| 2010/0307726 A1 | 12/2010 | Chiu et al. |
| 2011/0054226 A1* | 3/2011 | Kopkalli et al. .............. 570/175 |

OTHER PUBLICATIONS

Kirk-Othmer, Reactor technology, Encyclopedia of Chemical Technology (Third Edition), vol. 19, pp. 880-914, 1982, John Wiley & Sons.

* cited by examiner

COMBINATION REACTOR SYSTEM

BACKGROUND OF THE INVENTION

With the highly exothermic nature of some reactions, including the hydrogenation of certain fluorocarbons, there is a need to remove heat while a reaction progresses. Traditional shell-and-tube reactors often do not have enough heat transfer ability to keep the reaction systems at reasonable operating conditions. On the other hand, a purely trickle-bed reactor setup does not always provide enough ability to control both the temperature and/or reaction progression.

Generally, a shell-and-tube catalytic reactor is a type of reactor which is used to efficiently add or remove reaction heat. In some uses of these reactors, a catalyst is filled in a plurality of reaction tubes; a reaction fluid (gas and/or liquid) into the reaction tubes to cause a chemical reaction for obtaining a desired product; and a heat transfer medium is circulated through the reactor shell such that the chemical reaction can occur under controlled thermal conditions.

Shell and tube reactors typically include a number of reaction tubes held in place in the shell by one or more tubesheets; shell nozzles are used for introducing and withdrawing the heat transfer medium; tube nozzles are used for introduction of reactants into the reaction tubes and for withdrawing product therefrom; and appropriate dividers and/or baffles are used to separate the respective reactor parts for their specific functions.
The reactor parts are typically made from materials that do not react with the materials being processed in the reactor.

The term trickle bed reactor is used to describe a reactor in which a liquid phase and a gas phase flow concurrently downward through a fixed bed of catalyst particles while reaction takes place. At sufficiently low liquid and gas flow rates the liquid trickles over the packing in essentially a laminar film or in rivulets, and the gas flows continuously through the voids in the bed.

A useful general review of trickle bed reactors and other multiphase reactors can be found under the heading "Reactor Technology" in "Kirk-Othmer Encyclopedia of Chemical Technology", Third Edition, Volume 19, at pages 880 to 914. This reference states the following at page 892, "Trickle-bed reactors have complicated and as yet poorly defined fluid dynamic characteristics. Contacting between the catalyst and the dispersed liquid film and the film's resistance to gas transport into the catalyst, particularly with vapor generation within the catalyst, is not a simple function of liquid and gas velocities."

In operation, a typical trickle bed reactor has a fixed catalyst bed positioned vertically. A reaction mixture comprising a liquid, a gas or both, flows downwardly through the bed. The exothermic heat of reaction is absorbed by vaporizing a combination of reactant, product, by-product, and optionally solvent. For a reaction to occur, the reactants must diffuse into the liquid phase, then diffuse to the catalyst particles, and then react. The reaction products, if soluble in the liquid phase, are then removed from the reactor.

The total reaction mechanism in such a system thus includes the steps of diffusion and reaction. The reactants must diffuse into the liquid phase and then diffuse to the catalyst particles, and the reaction rate is thus affected by the rate of diffusion to the catalyst particles. Assuming a situation where the catalytic reaction occurs at the surface of the catalyst particles, the reaction rate is affected further by the reaction rate constant, the concentration of the reactants at the particle surface, and the surface area of the catalyst particles. The resulting reaction products must then diffuse away from the catalyst particles and back to the mainstream liquid flow. Accordingly, the final reaction rate, as controlled by the slowest of the aforementioned steps, and is affected most by either the rate at which catalysis proceeds or the rate at which diffusion of the reactants and the products proceeds. The primary resistance to diffusion occurs at boundary layer areas, and thus it would be advantageous to increase both the gas and the liquid flow rates to decrease such boundary layers.

PRIOR ART

The following prior art documents are hereby incorporated herein by reference in their entirety.

U.S. Pat. No. 3,566,961 is entitled "tubular reactor for carrying out endothermic and exothermic reactions with forced circulation." This patent teaches a tubular reactor with forced circulation of a heat transfer medium which flushes the outside of the reaction tubes in axial direction, the heat transfer medium being supplied to, and withdrawn from, the reactor wall uniformly through circular pipelines, and particularly the constructional shape of deflecting guide plate means arranged transversely to the direction of flow and having annular openings around the reaction tubes for uniform flow towards all the tubes of the nest of tubes.

U.S. Pat. No. 3,792,980 is entitled "reactor for carrying out reactions accompanied by a change in heat." This patent teaches a shell and tube reactor for reactions accompanied by a change in heat. Reaction material flows through the tubes and a heat exchange medium flow through the shell to remove or supply heat of the reaction. Also a pump disposed in the reactor on the shell side circulates the heat exchange medium within the shell. The tubes are disposed in spaced sectors so that passageways are provided for the circulating heat exchange medium. Heat exchange medium is withdrawn and supplied to the shell and is itself subjected to heat exchange outside the reactor. Improved distribution of the heat exchange medium within the shell is obtained by withdrawing and supplying the heat exchange medium, respectively, from and to the aforesaid passageways.

U.S. Pat. No. 4,101,287 is entitled "combined heat exchanger reactor." This patent teaches a one-piece, integral, high strength, combined heat exchanger-reactor comprising a monolithic honeycomb structure wherein the channels thereof are divided into two or more groups; group one carrying one fluid and group two carrying another fluid which differs from the first in composition and/or temperature and/or pressure and/or direction of flow, the main design feature of the combined heat exchanger-reactor (CHER) being that group one channels extend outward parallel to the channel axis and perpendicular to the cross-section of the honeycomb and each channel of this group one being in thermal contact through common walls with channels of group two while each channel of group one is separated from other channels of group one by the intervening voids formed by the presence of the channels of group two.

U.S. Pat. No. 4,929,798 is entitled "pseudoadiabatic reactor for exothermal catalytic conversions." This patent teaches a multitubular catalytic reactor for exothermal catalytic reactions comprises a bundle of parallel tubes all of the same length and a catalyst within the tubes. The tube bundle has an inlet side and an outlet side. Devices are provided for introducing separately reactants to within the tubes of the reactor and coolant to the channels defined between adjacent tubes of the bundle. The coolant is introduced into the channels co-currently with the direction of flow of the reactants. The products are withdrawn from the tubes independently of the coolant.

U.S. Pat. No. 5,027,891 is entitled "method for transferring heat between process liquor streams." This patent teaches a method of transferring heat between process liquor streams such as streams of caustic liquor in the Bayer process for producing alumina from bauxite, utilizing a heat pipe arrangement for heat exchange. The process streams respectively pass in contact with one surface of a first heat-exchange wall and one surface of a second heat-exchange wall while being isolated from the second surfaces of the two walls; these second walls are exposed to a closed volume (also isolated from both process streams) containing a heat transfer fluid that vaporizes below the temperature of the hotter process stream and condenses above the temperature of the cooler process stream. The heat transfer fluid vaporizes at the exposed surface of the wall contacted by the hotter stream, and condenses at the exposed surface of the wall contacted by the cooler stream, thereby transferring heat (as heat of vaporization) from the former stream to the latter.

U.S. Pat. No. 6,180,846 is entitled "process and apparatus using plate arrangement for combustive reactant heating." This patent teaches a process and apparatus for indirectly heating an endothermic reaction by combustion of reactants or products from the endothermic reaction using a plate heat exchange arrangement in a highly efficient manner. This invention is particularly suited for processes such as the production of styrene or synthesis gas.

U.S. Pat. No. 6,790,431 is entitled "reactor for temperature moderation." This patent teaches embodiments which include methods and apparatus for arranging multiple reaction zones such that at least one hot spot in one of the reaction zones is moderated by a cooler spot in an adjacent reaction zone.

U.S. Pat. No. 7,521,028 is entitled "catalytic reactor for low-Btu fuels." This patent teaches an improved catalytic reactor which includes a housing having a plate positioned therein defining a first zone and a second zone, and a plurality of conduits fabricated from a heat conducting material and adapted for conducting a fluid therethrough.

SUMMARY OF THE INVENTION

The present invention is directed to a combination reactor system for exothermic reactions comprising a trickle-bed reactor and a shell-and-tube reactor. This combination allows the system to efficiently remove heat while also providing the ability to control both the temperature and/or reaction progression. The trickle-bed reactor removes heat efficiently from the system by utilizing latent heat and does not require the use of a cooling or heating medium. The shell-and-tube reactor is used to further progress the reaction and provides a heat exchanger in order to introduce fluid at the desired temperature in the shell-and-tube reactor. Also, additional reactant or reactants and/or other fluids may be introduced to the shell-and-tube section of the reactor under controlled temperature conditions.

These reactors can be separated by a heat exchanger in order to introduce fluid at the desired temperature to the shell-and-tube reactor. Also, additional reactant or reactants and/or other fluids may be introduced to the shell-and-tube section of the reactor.

The trickle-bed and shell-and-tube or trickle-bed, heat exchanger, and shell-and-tube setup can be connected in a way so as to provide the optimal system for reaction progress and heat exchange as required by any process. For instance, the pieces of equipment could be stacked with the trickle-bed reactor on top and shell-and-tube reactor on the bottom. This saves floor space.

The trickle-bed reactor would be similar to the trickle-bed normally used in chemical engineering with a fixed bed or reactor catalyst and two phases present in the reactor.

The shell-and-tube reactor could be a multi-stage, multi-tube, shell-and-tube heat exchanger which contains reactor catalyst in certain tubes and optionally, no catalyst in other tubes. See, for example, U.S. Patent Pub. Nos. 2011-0054226 and 2010-0307726, the disclosures of which are hereby incorporated herein by reference.

If desired, a simpler shell-and-tube reactor design could be provided depending on the systems requirements. The heat exchanger could be a traditional heat exchanger used for removing or adding heat or causing a phase change of the process fluid.

DETAILED DESCRIPTION OF THE INVENTION

As described above, the present invention is directed to a combination reactor system comprising a trickle-bed reactor connected to a shell-and-tube reactor. This reactor combination is especially useful for conducting exothermic reactions, i.e., reactions that are accompanied by the evolution of heat as the reaction occurs. Highly exothermic reactions, i.e., reactions that produce high temperatures can be safely conducted in the combination reactor system of the present invention. Typically, hydrogenation, oxidation and chlorination are recognized as highly exothermic reactions.

This system allows the reaction operators to efficiently add and/or remove heat from the reaction system while also providing the ability to control both the temperature and/or reaction progression. The trickle-bed reactor removes heat efficiently from the system by utilizing latent heat and does not require a cooling or heating medium. The shell-and-tube reactor is used to further progress the reaction and to provide rapid heat exchange ability should the reaction progress not be meeting desired requirements.

Figure 1:
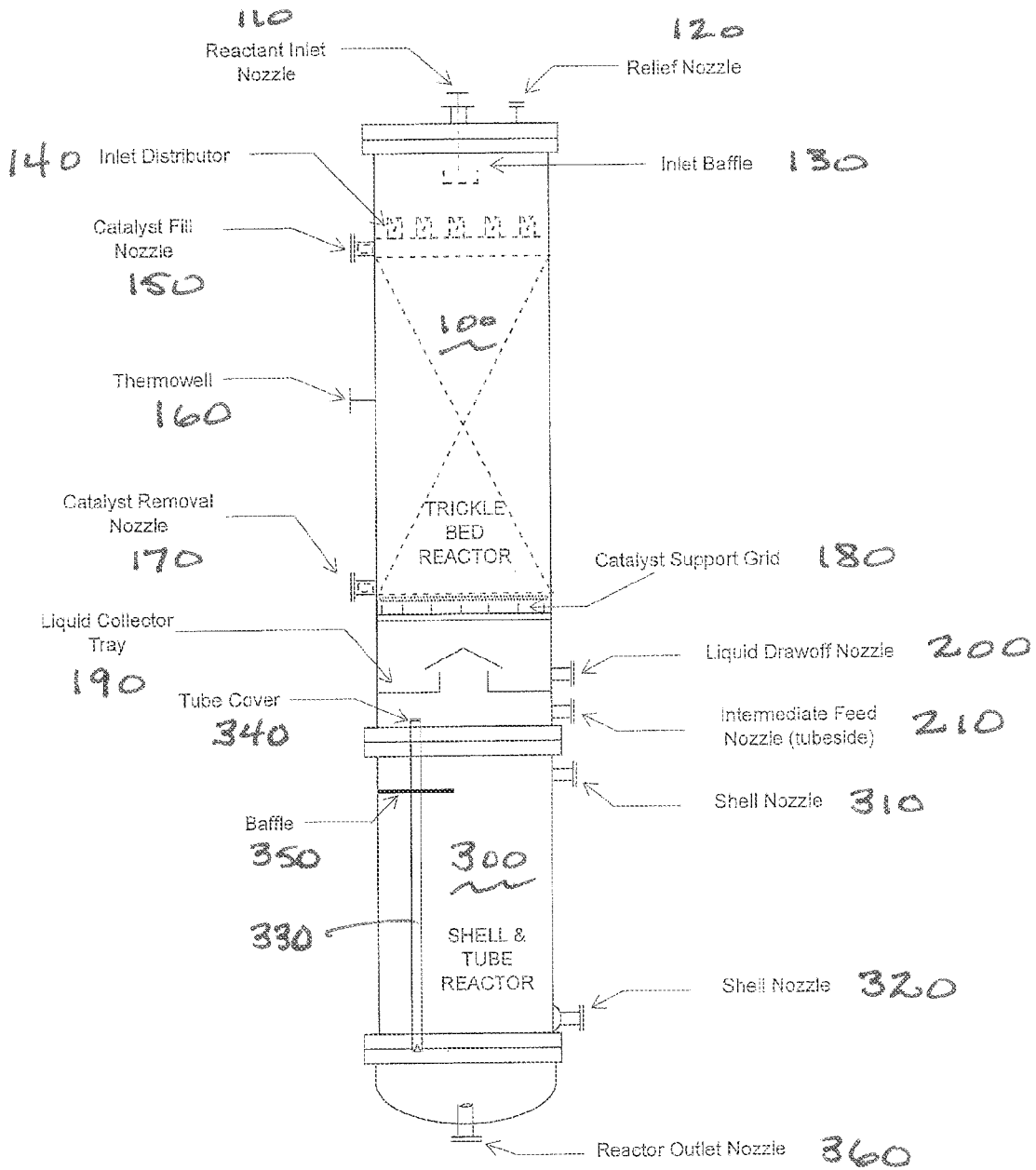
FIG. 1 illustrates one embodiment of the combination reactor system of the present invention, showing a combined trickle bed reactor and a shell and tube reactor system.
Figure 2:
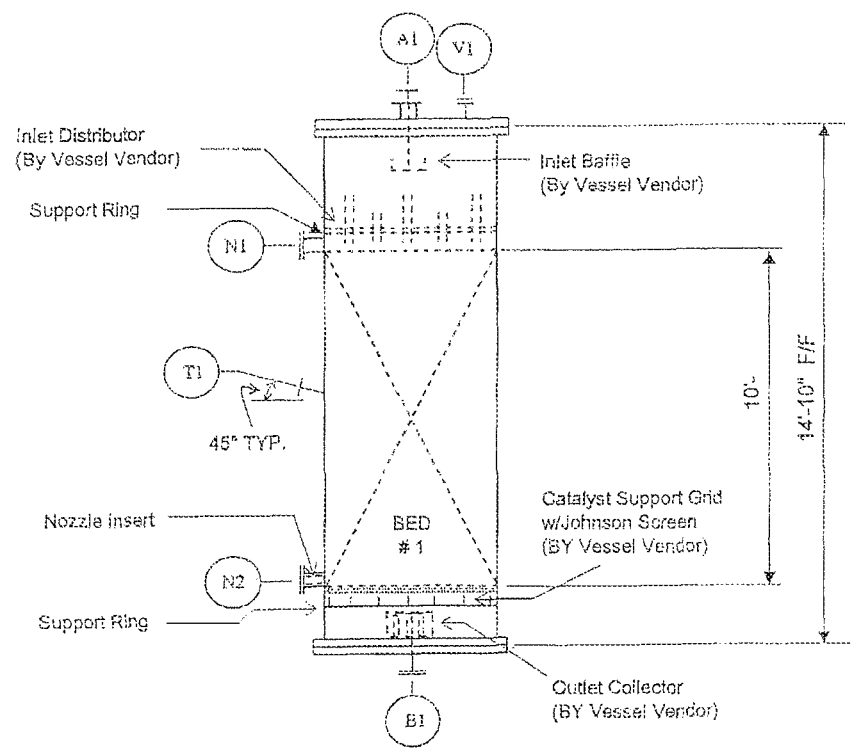
FIG. 2 illustrates one embodiment of a trickle bed reactor useful in the combination reactor system of the present invention.
Figure 3:
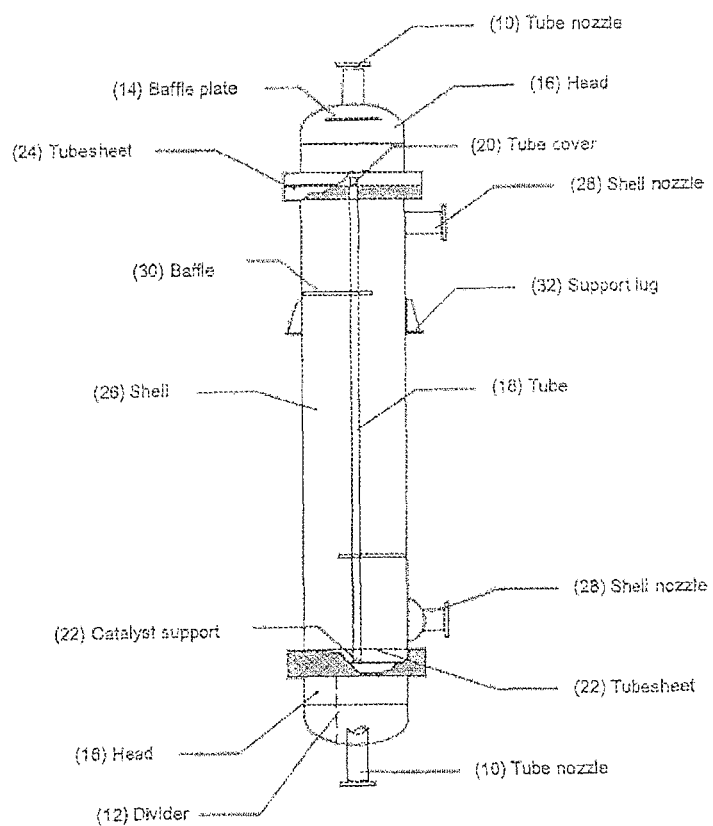
FIG. 3 illustrates one embodiment of a shell and tube reactor useful in the combination reactor system of the present invention.

As illustrated in FIGS. 1, 2 and 3, the combination reactor system of the present invention comprises a trickle-bed reactor followed by a shell-and-tube reactor. This system allows highly exothermic and/or highly endothermic reactions to precede under the precise control of the system operators, as the combined reactor system allows for the efficient addition and/or removal of heat from the reaction, while also providing the ability to control both the temperature and/or reaction progression.

FIG. 1 illustrates one embodiment of a combination reactor system of the present invention, comprising a trickle-bed reactor 100 mounted to a shell-and-tube reactor 300. As shown therein, the upper reactor is the trickle bed reactor 100. This reactor includes a reactant inlet nozzle 110 and a relief nozzle 120 at the top part of the reactor. Internally, this reactor includes an inlet baffle 130 and an inlet distributor 140. Also shown are the catalyst fill nozzle 150, a thermowell 160, a catalyst removal nozzle 170, and a catalyst support grid 180.

A liquid collector tray 190, is placed between the between the two reactor sections. Gas will continue to flow down to the shell & tube reactor, whereas liquid product may be optionally withdrawn from the system via liquid drawoff nozzle 200. Should any additional reactants be required at this stage of the processing, they may be added via intermediate feed nozzle 210.

As further illustrated in FIG. 1, the bottom portion of the combination reactor system of the present invention includes the shell and tube reactor 300. This reactor includes an upper shell nozzle 310 and a lower shell nozzle 320. One of the multiple reactor tubes 330 is shown in the reactor, and each tube includes a tube cover 340. The tubes are positioned in the reactor with a baffle 350. The reactor outlet nozzle 360 is shown at the bottom.

The trickle-bed removes reaction heat efficiently from the system by utilizing latent heat and does not require a cooling or heating medium. One embodiment of such a reactor is shown in FIG. 2. As shown therein, the reactor includes a bed of catalyst, and various inlet and outlet ports, baffles and distributors for conducting reactions therein.

As illustrated in FIG. 2, the reactor includes the following components;

A1—reactant inlet nozzle
V1—relief nozzle
N1—catalyst fill nozzle
T1—thermowell
N2—catalyst (HK) outlet nozzle
B1—reactor outlet nozzle The shell-and-tube reactor is used to further progress the reaction and to provide heat exchange ability should the reaction progress past the desired process design. One embodiment of such a reactor is shown in FIG. 3. As shown therein, the reactor includes tubes of supported catalyst, and various inlet and outlet ports, baffles and distributors for conducting reactions therein.

As illustrated in FIG. 3, the reactor includes the following;

10—Tube nozzle
12—Divider
14—Baffle Plate
16—Head
18—Tube
20—Tube cover
22—Catalyst support
24—Tubesheet
26—Shell
28—Shell nozzle
30—Baffle
32—Support lug As described above, if desired these reactors can be separated by a heat exchanger in order to introduce fluid at the desired temperature to the shell-and-tube reactor.

If desired, additional reactant or reactants and/or other fluids may be introduced to the shell-and-tube section of the reactor.

The trickle-bed and shell-and-tube or trickle-bed, heat exchanger, and shell-and-tube setup can be done in a way so as to provide the optimal system for reaction progress and heat exchange as required by any process.

In one embodiment, the pieces of equipment are stacked with the trickle-bed reactor on top and shell-and-tube reactor on the bottom; thereby preserving floor space. Here, the trickle bed reactor is similar to the trickle-bed normally used in chemical engineering with a fixed bed of reactor catalyst and two phases in the reactor. The shell-and-tube reactor is a multi-stage, multi-tube, multi-heating zone, shell-and-tube heat exchanger which contains reactor catalyst in certain tubes and optionally, no catalyst in other tubes. See U.S. Patent Pub. No. 2010-0307726 A1. For another preferred design, see U.S. Patent Pub. No. 2011-0054226 A1.

However, a simpler shell-and-tube reactor design could be used, depending on the reaction and/or systems requirements. The heat exchanger could be a traditional heat exchanger used for removing or adding heat or causing a phase change of the process fluid. Even in the case of a traditional shell & tube reactor, some or all of the tubes may be filled with catalyst.

As described above, the present invention is preferably designed for use with exothermic reactions. For example, reactions involving the catalytic hydrogenation of fluoro-olefins are typically exothermic, and these reactions are one preferred type of reaction that may be conducted in the combination reactor of the present invention. In such a case the reactor should be constructed from materials which are resistant to the corrosive effects of the reagents employed therein. Typical materials for the reactors include metals such as nickel and its alloys, including Hastelloy, Inconel, Incoloy, and Monel or vessels lined with fluoropolymers. Other suitable materials used under suitable conditions could be steel or stainless steel.

The process flow may either be in the down or up direction through a bed of the catalyst in the shell and tube reaction zones. If the reaction zones require heating for optimal reaction, one or more of the temperature control zones is charged with a heating medium that provides sufficient heat to the reaction zones to provide the desired reaction temperature. Materials suitable for use as a heating medium are well known to persons having ordinary skill in this art, and include for example, hot tempered water, hot oil, and condensing steam. Similarly, if the reaction zones require cooling to maintain optimal reaction conditions, one or more of the temperature control zones is charged with a suitable cooling medium that removes heat and achieves or maintains the desired temperature in the reaction zones. Materials suitable for use as a cooling medium are well known to persons having ordinary skill in this art, and include for example, cooling water and boiling water.

In commercial processes where a fluoro-olefin $C_nH_{(2n-x)}F_{(x)}$ to $C_{(n)}H_{(2n-x+2)}F_{(x)}$ is hydrogenated (e.g., hexafluoropropylene to 236ea, 1225ye to 245eb, and the like), inadequate management or control of heat removal may induce excess hydrogenation, decomposition and hot spots resulting in reduced yields and potential safety issues. In the hydrogenation of fluoro-olefins, it is therefore necessary to control the reaction temperature as precisely as practical to overcome challenges associated with heat management and safety.

REACTION EXAMPLES

Particularly useful reactions to make use of this invention include the following:

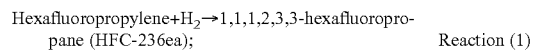

Reaction (1)

and

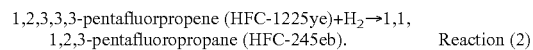

Reaction (2)

Note, an undesired over-hydrogenation product in Reaction (2) is 1,1,1,2-tetrafluoro-propane (HFC-254eb).

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A method of performing exothermic reactions, wherein the reactions comprise the hydrogenation of one or more fluorocarbon compounds, the method comprising the steps of,
    (a) first conducting said exothermic reactions in an upstream trickle-bed reactor which does not include a heating or cooling medium to produce a trickle-bed reactor effluent, and
    (b) thereafter conducting said exothermic reactions on at least a portion of the trickle-bed reactor effluent from step (a) in a downstream shell-and-tube reactor which comprises a temperature control system selected from the group consisting of a heating medium, a cooling medium, and both a heating and a cooling medium,
    wherein the reactors used in steps (a) and (b) are separated by a heat exchanger, thereby permitting the introduction of reactants to the shell-and-tube reactor at any desired temperature; and
    wherein the combination of steps (a) and (b) provide for both efficient removal of heat and further provide control of the exothermic reaction temperature and the reaction progression, thereby reducing or eliminating the formation of undesired over-hydrogenation products.

2. The method of claim 1, wherein the reactors of steps (a) and (b) are stacked with the trickle-bed reactor on top and shell-and-tube reactor on the bottom.

3. The method of claim 1, wherein the trickle bed reactor comprises a fixed bed of reactor catalyst and two phases in the reactor.

4. The method of claim 1, wherein the shell-and-tube reactor comprises a multi-stage, multi-tube, shell-and-tube heat exchanger which contains reactor catalyst in at least some of the tubes.

5. The method of claim 4, wherein the shell-and-tube reactor has catalyst in all tubes.

6. The method of claim 1, wherein the heat exchanger is used for removing or adding heat or causing a phase change of a reaction medium.

7. The method of claim 1, wherein the trickle-bed reactor removes heat efficiently from the system by utilizing latent heat.

8. The method of claim 1, wherein the hydrogenation reaction comprises the conversion of hexafluoropropylene to 1,1,1,2,3,3-hexafluoropropane.

9. The method of claim 1, wherein the hydrogenation reaction comprises the conversion of 1,2,3,3,3-pentafluorpropene to 1,1,1,2,3-pentafluoropropane.

10. A method of performing exothermic reactions, wherein the reactions comprise the hydrogenation of one or more fluorocarbon compounds, the method comprising the steps of,
    (a) first conducting said exothermic reactions in a trickle-bed reactor which does not include a heating or cooling medium to produce a trickle-bed reactor effluent, and
    (b) thereafter conducting said exothermic reactions on the trickle-bed reactor effluent from step (a) in a downstream shell-and-tube reactor which comprises a shell structure and a tubesheet located in the shell structure;
    wherein the tubesheet comprises one or more reaction zones and one or more temperature control zones, wherein each reaction zone comprises a plurality of aligned reaction tubes; and
    each temperature control zone comprises a plurality of aligned temperature control tubes;
    wherein the reactors used in steps (a) and (b) are separated by a heat exchanger, thereby permitting the introduction of reactants to the shell-and-tube reactor at any desired temperature; and
    wherein the combination of steps (a) and (b) provide for both efficient removal of heat and further provide control of the exothermic reaction temperature and the reaction progression, thereby reducing or eliminating the formation of undesired over-hydrogenation products.

* * * * *